United States Patent
Villamil et al.

(10) Patent No.: US 12,137,946 B2
(45) Date of Patent: Nov. 12, 2024

(54) SPINAL PLATE

(71) Applicant: AEGIS SPINE, INC., Englewood, CO (US)

(72) Inventors: Fernando L. Villamil, Englewood, CO (US); Larry T. Khoo, Englewood, CO (US); Youngbo Ahn, Englewood, CO (US); Jae Shik Lee, Englewood, CO (US)

(73) Assignee: AEGIS SPINE, INC., Englewood, CO (US)

( * ) Notice: Subject to any disclaimer, the term of this patent is extended or adjusted under 35 U.S.C. 154(b) by 666 days.

(21) Appl. No.: 17/412,820

(22) Filed: Aug. 26, 2021

(65) Prior Publication Data

US 2021/0386458 A1   Dec. 16, 2021

Related U.S. Application Data

(63) Continuation-in-part of application No. 16/821,321, filed on Mar. 17, 2020, now Pat. No. 11,129,650.

(51) Int. Cl.
*A61B 17/70* (2006.01)
*A61B 17/86* (2006.01)

(52) U.S. Cl.
CPC ...... *A61B 17/7058* (2013.01); *A61B 17/8695* (2013.01)

(58) Field of Classification Search
CPC ................ A61B 17/7058; A61B 17/8695
See application file for complete search history.

(56) References Cited

U.S. PATENT DOCUMENTS

| | | | |
|---|---|---|---|
| 5,451,226 A | 9/1995 | Pfeil et al. | |
| 9,068,382 B1 | 6/2015 | Hall | |
| 11,129,650 B1* | 9/2021 | Villamil | A61B 17/7058 |
| 2002/0078529 A1 | 6/2002 | Schwarz | |
| 2005/0006432 A1 | 1/2005 | Racenet et al. | |

(Continued)

FOREIGN PATENT DOCUMENTS

| | | |
|---|---|---|
| JP | 2014-516607 A | 7/2014 |
| WO | 9531941 A1 | 11/1995 |

OTHER PUBLICATIONS

International Search Report and Written Opinion dated Nov. 22, 2022, issued in counterpart International Application No. PCT/IB22/57983. (9 pages).

(Continued)

*Primary Examiner* — Nicholas J Plionis
(74) *Attorney, Agent, or Firm* — WHDA, LLP

(57) ABSTRACT

The present invention provides a spinal plate which is used to perform fixation surgery on a spine in orthopedic surgery and neurosurgery. The spinal plate comprises a central body and a pair of rotation portions which are disposed on both sides in a longitudinal direction of the central body and each of the pair of rotation portions has bone screw. The spinal plate also comprises spike screw in each of the pair of rotation portions. Each of the pair of rotation portions include a rotation connection portion, and the central body includes a rotation support portion. Rotation pins are used to connect the central body with the pair of rotation portions disposed on both sides in a longitudinal direction of the central body and enable the pair of rotation portions to rotate clockwise or counterclockwise with respect to the central body.

13 Claims, 15 Drawing Sheets

(56) References Cited

U.S. PATENT DOCUMENTS

| | | |
|---|---|---|
| 2005/0228376 A1 | 10/2005 | Boomer et al. |
| 2006/0058819 A1 | 3/2006 | Kasic et al. |
| 2006/0142767 A1 | 6/2006 | Green et al. |
| 2007/0055239 A1 | 3/2007 | Sweeney et al. |
| 2007/0233116 A1* | 10/2007 | Olerud ............... A61B 17/8047 606/86 A |
| 2007/0233122 A1 | 10/2007 | Denis et al. |
| 2007/0270840 A1 | 11/2007 | Chin et al. |
| 2009/0157121 A1 | 6/2009 | Harris et al. |
| 2013/0060283 A1 | 3/2013 | Suh et al. |
| 2013/0090688 A1 | 4/2013 | Montello et al. |
| 2014/0200670 A1 | 7/2014 | Chin et al. |
| 2014/0268059 A1 | 9/2014 | Hosoki |
| 2014/0355374 A1 | 12/2014 | Huang et al. |
| 2015/0342648 A1 | 12/2015 | McCormack et al. |
| 2017/0311985 A1 | 11/2017 | Bobbitt et al. |
| 2018/0235671 A1* | 8/2018 | Jackson, III ....... A61B 17/7059 |
| 2021/0022777 A1 | 1/2021 | Jackson, III |

OTHER PUBLICATIONS

Dewell, "180 Degree Folding Flip Top Hinges," May 7, 2019 retrieved from https://www.amazon.com/Dewell-Degree-Folding-Hinges-Machine/dp/B07QQPY8JW. (1 page).

Office Action dated Jan. 25, 2022, issued in counterpart JP Application No. 2021-017271, with English Translation. (10 pages).

Notification Concerning Transmittal of International Preliminary Report on Patentability (Chapter 1 of the PCT) dated Mar. 7, 2024, issued in counterpart International Application No. PCT/IB2022/057983. (1 pages).

International Preliminary Report on Patentability (Chapter 1 of the PCT) dated Feb. 27, 2024, issued in counterpart International Application No. PCT/IB2022/057983. (1 pages).

* cited by examiner

[FIG. 1]
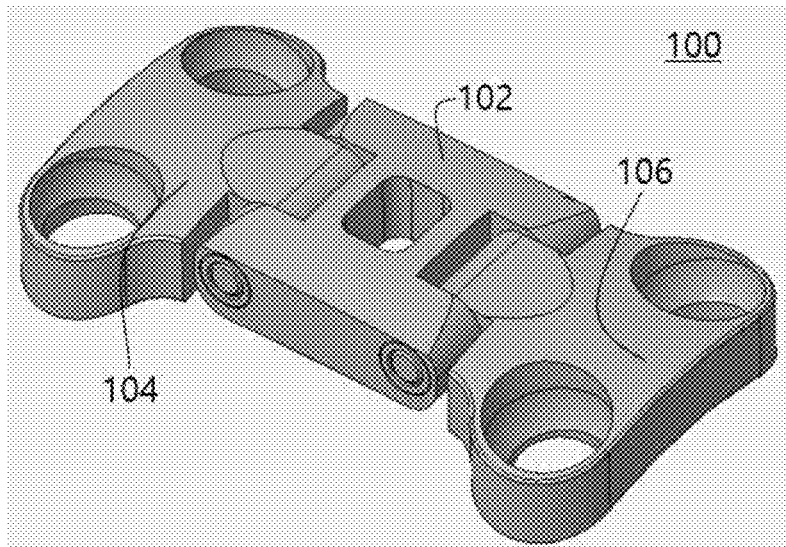
[FIG. 2]
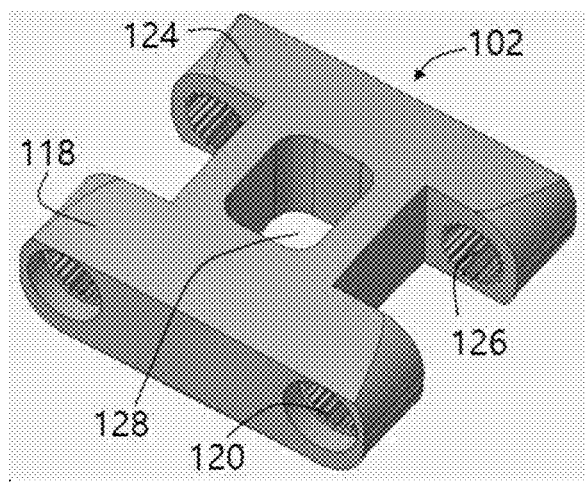

[FIG. 3]
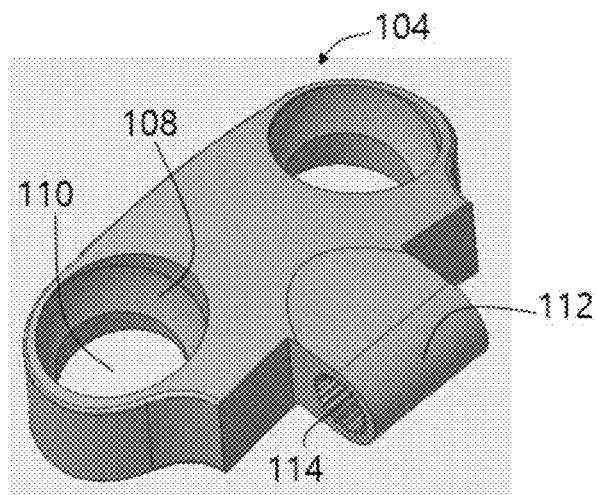
[FIG. 4]
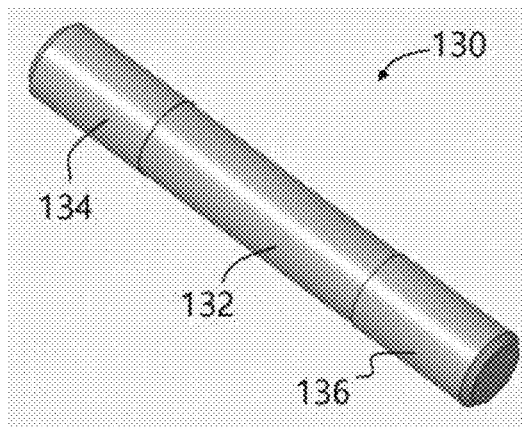

[FIG. 5]
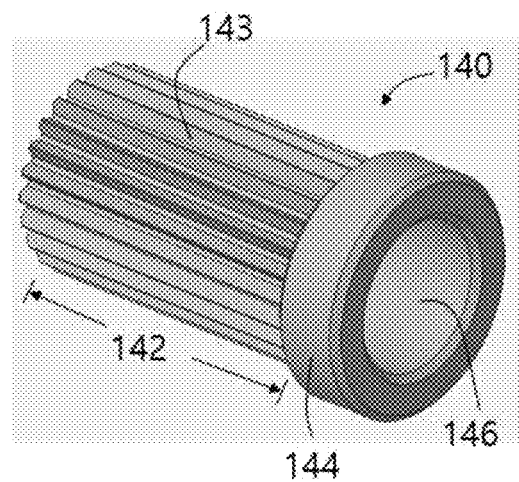
[FIG. 6]
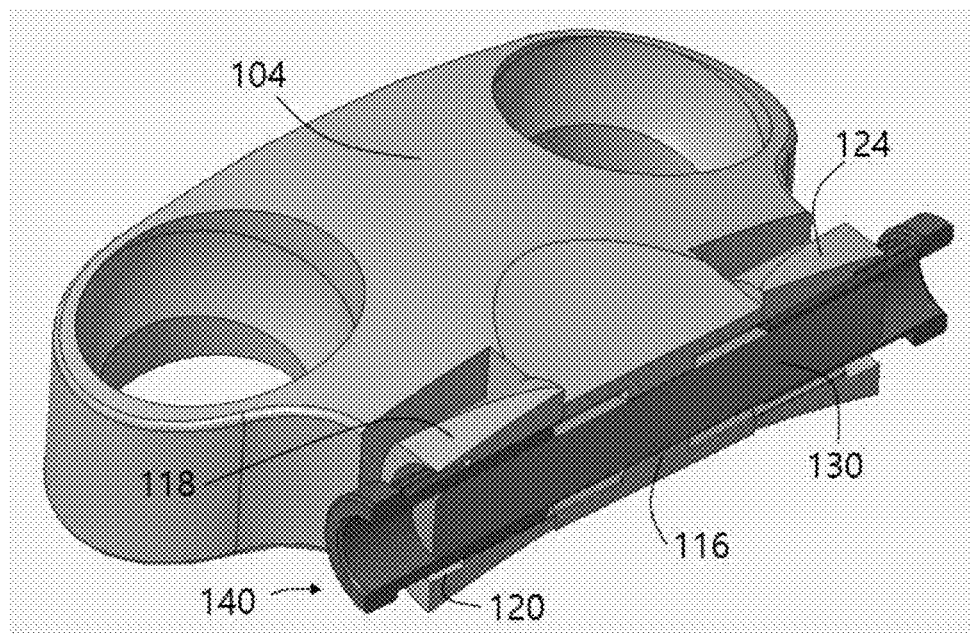

[FIG. 7]
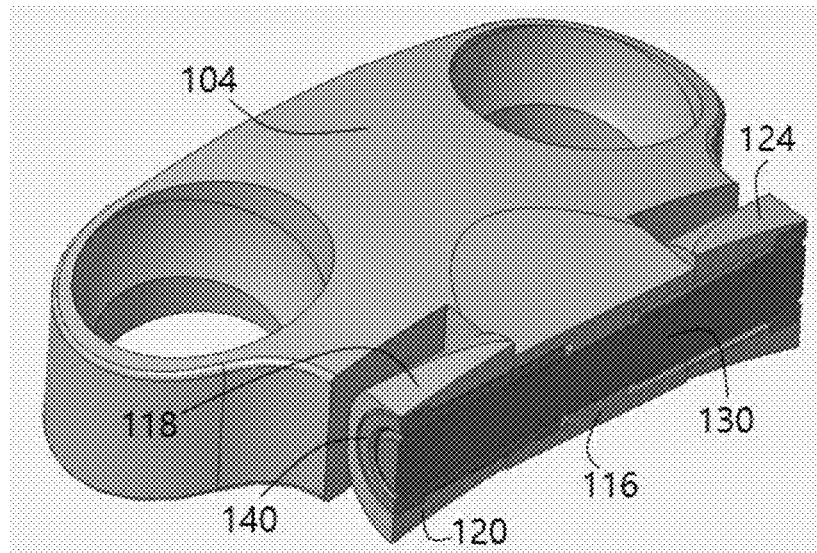
[FIG. 8]
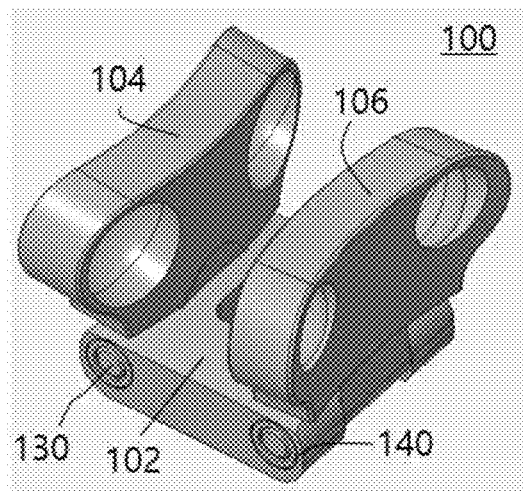

[FIG. 9]
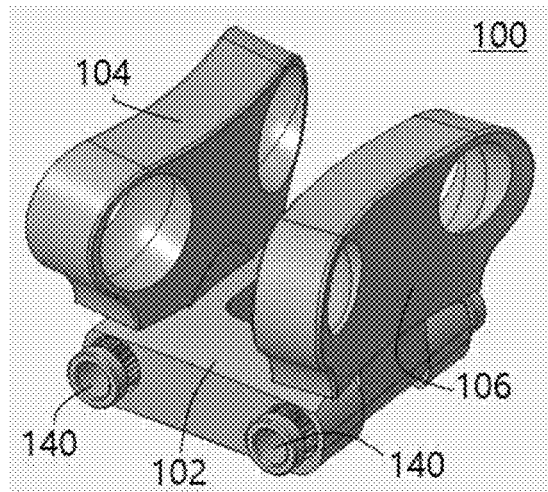
[FIG. 10]
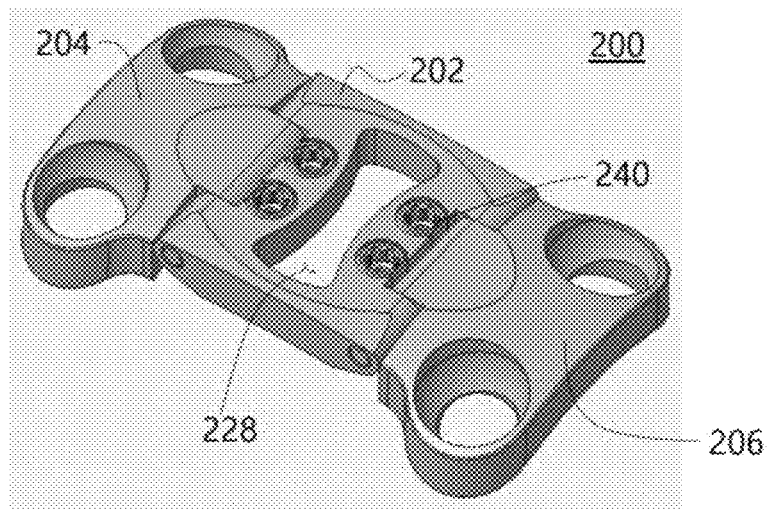

[FIG. 11]
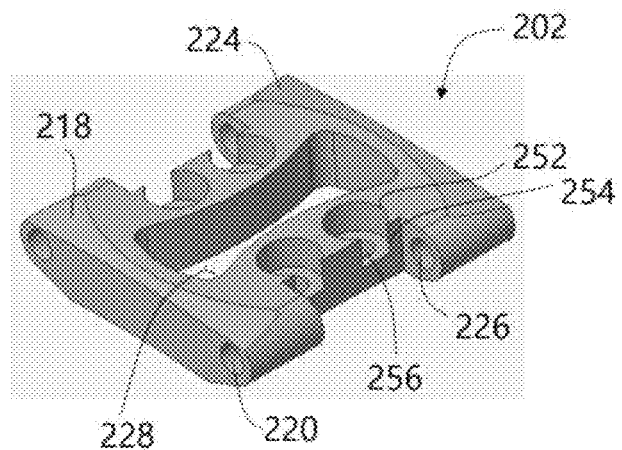
[FIG. 12]
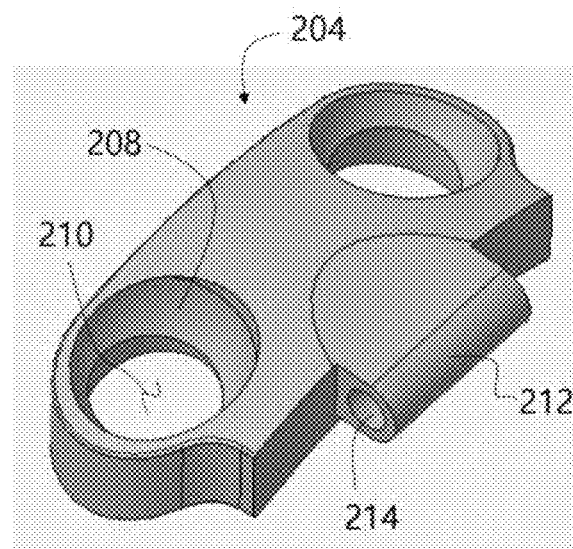

[FIG. 13]
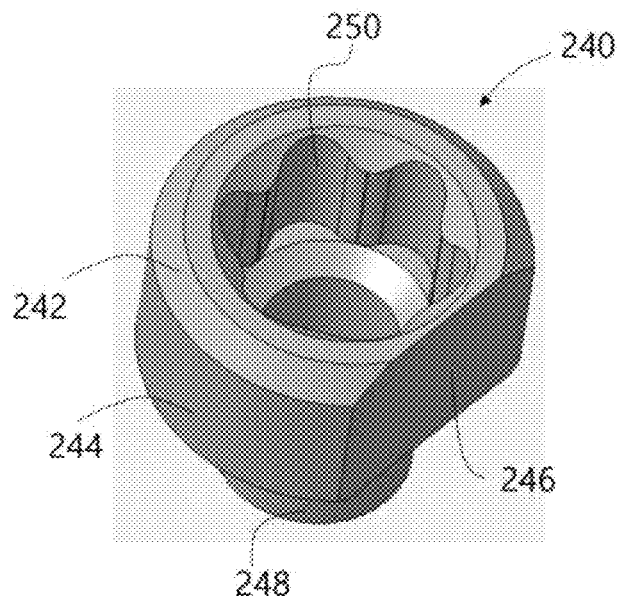
[FIG. 14]
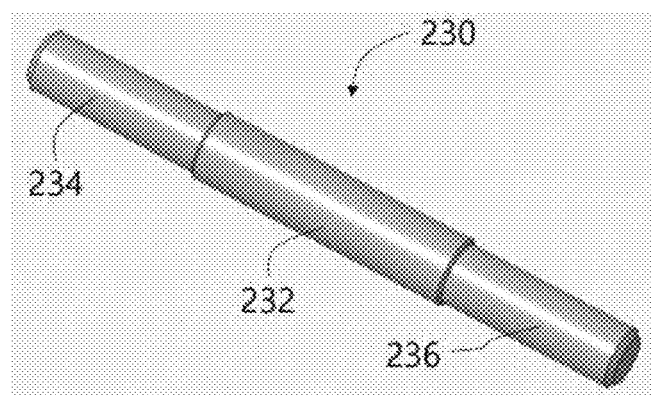

[FIG. 15]
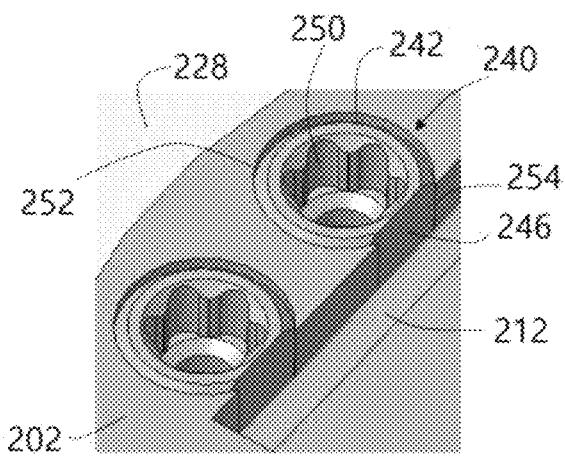
[FIG. 16]
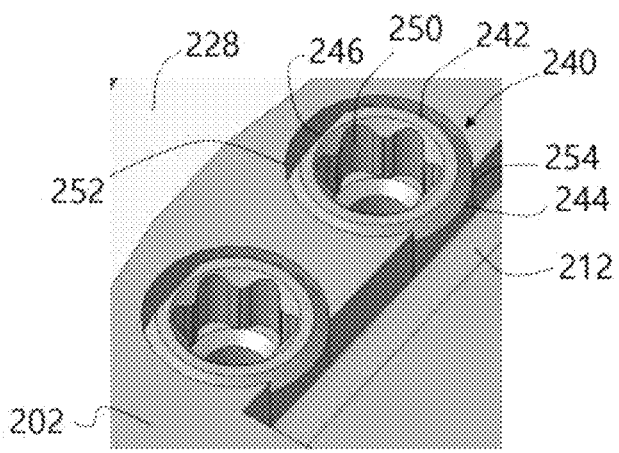

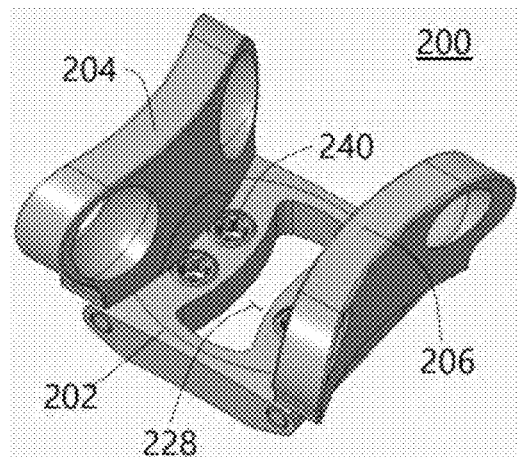
[FIG. 17]

[FIG. 18]
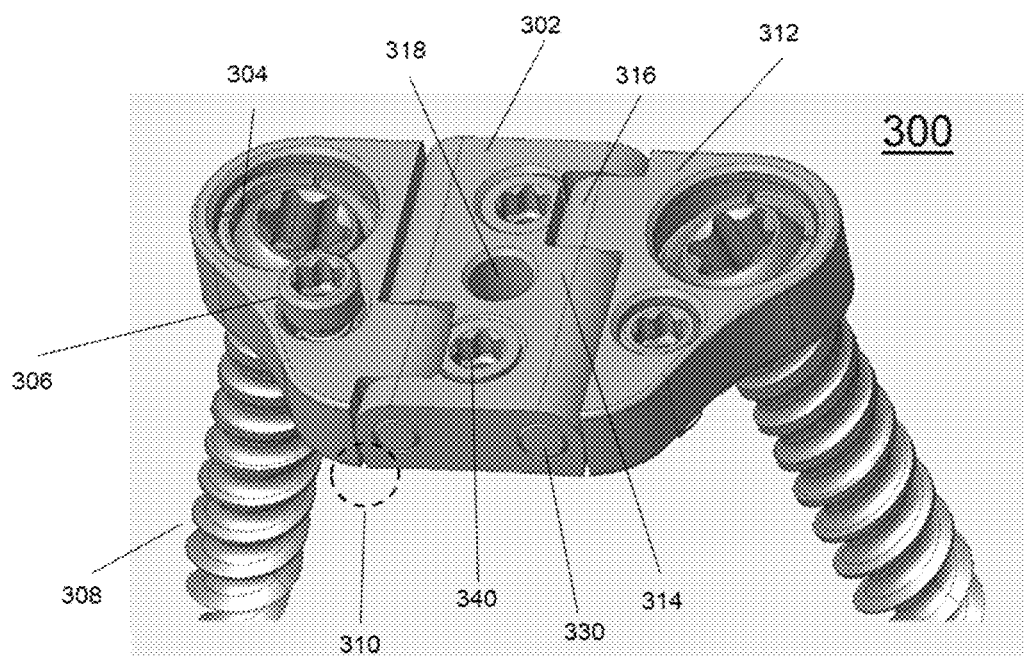

[FIG. 19]
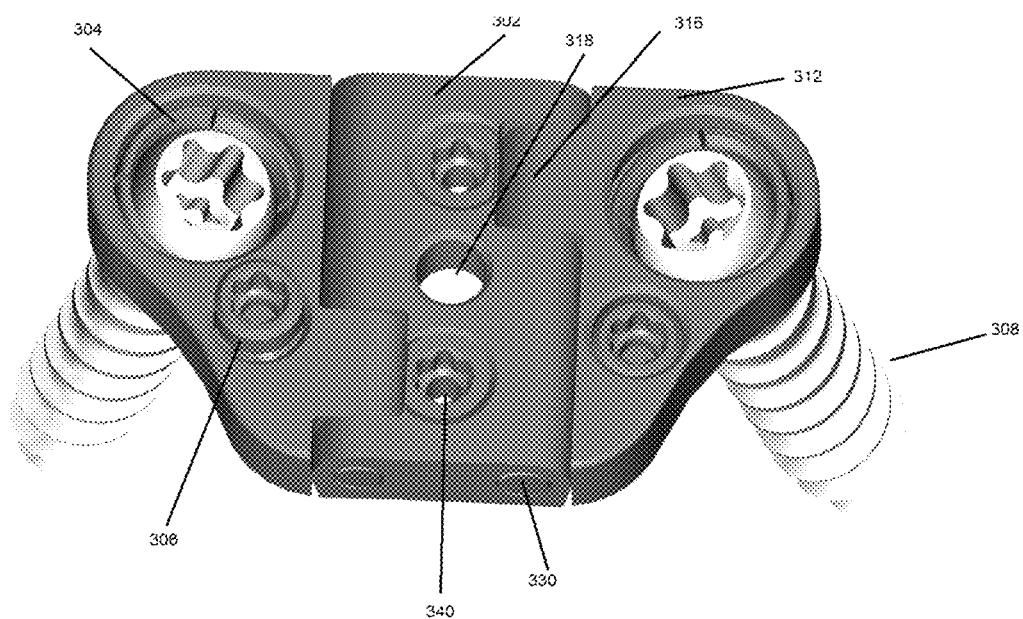

[FIG. 20]
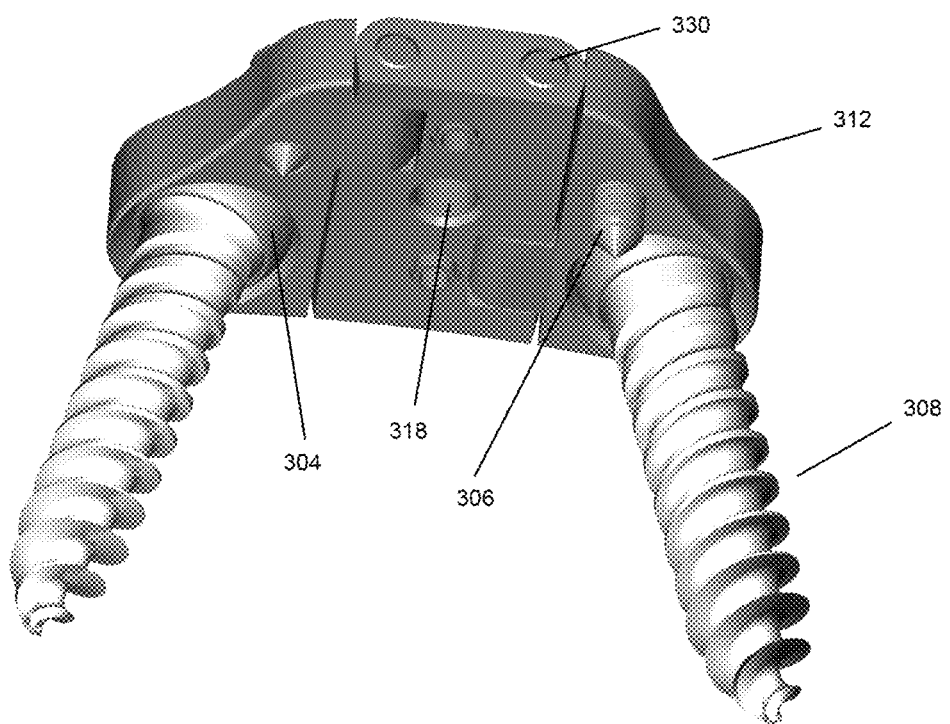

[FIG. 21]
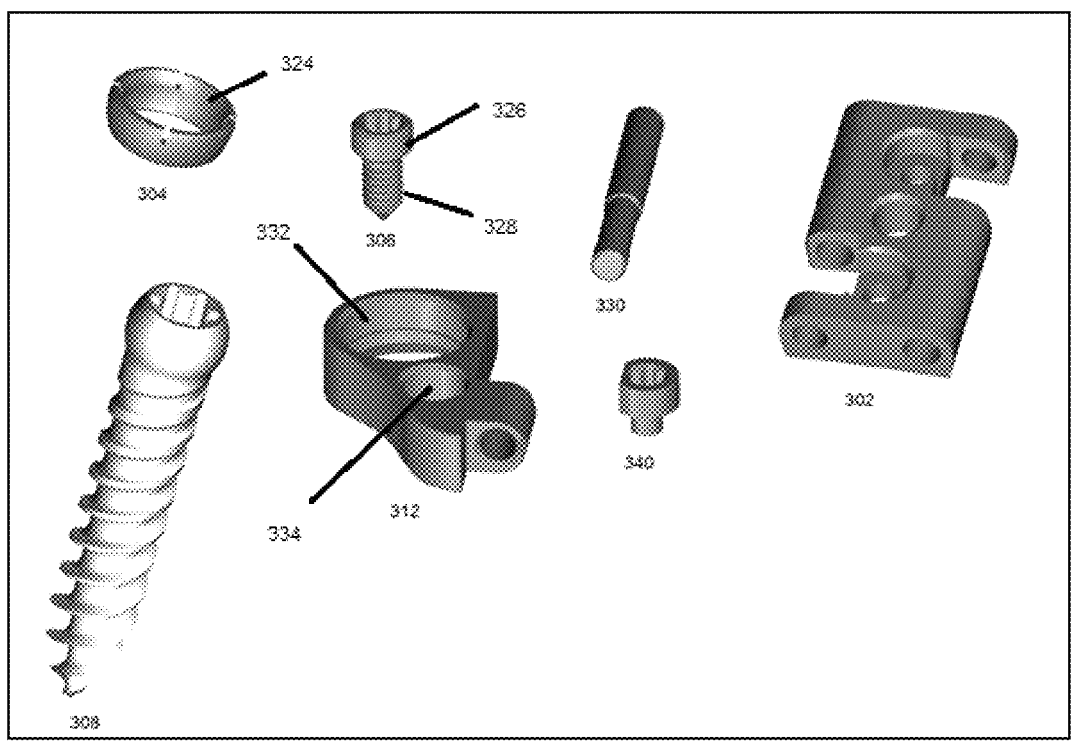

[FIG. 22]
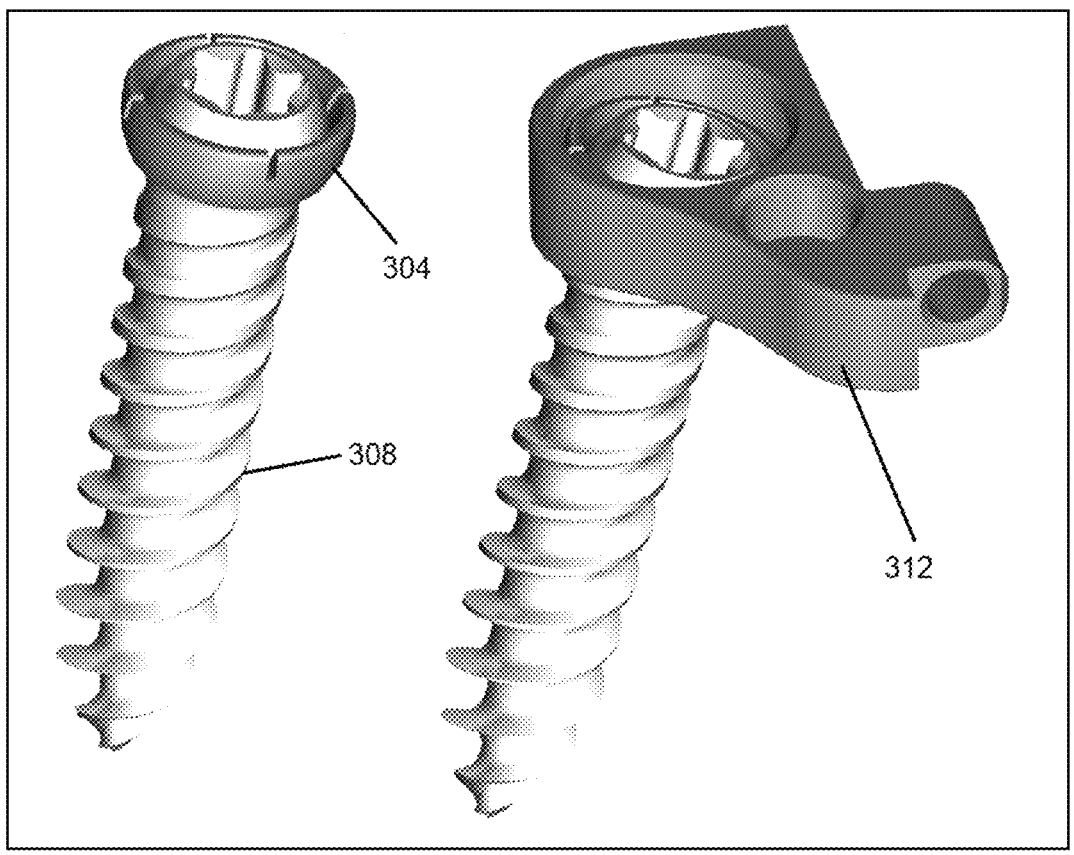

[FIG. 23]
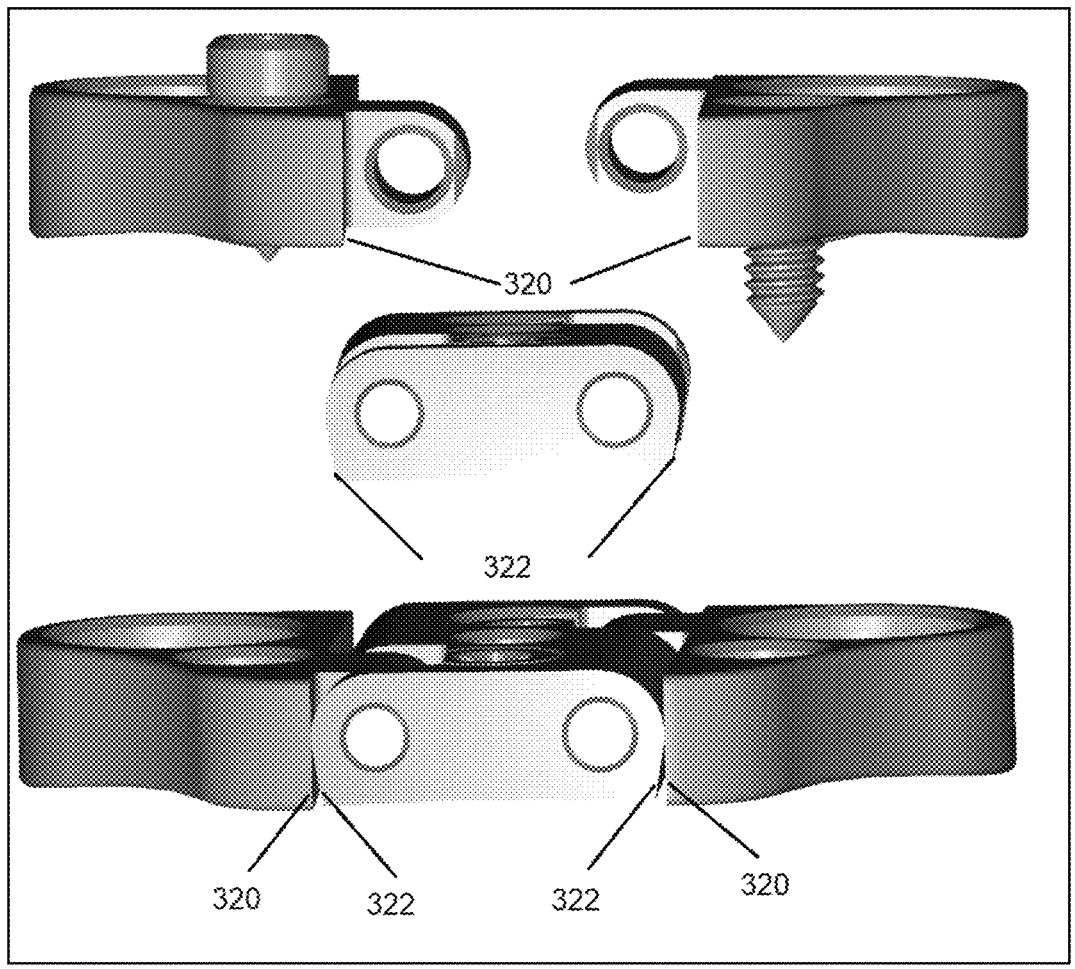

SPINAL PLATE

CROSS-REFERENCE TO RELATED APPLICATIONS

This application is a continuation-in-part application of U.S. patent application Ser. No. 16/821,321, filed on Mar. 17, 2020, and the content of the aforementioned application is incorporated herein by reference in their entirety.

BACKGROUND OF THE INVENTION

1. Field of the Invention

The present invention relates to a spinal plate, and more specifically to a spinal plate which is used to perform fixation surgery on a spine in orthopedic surgery and neurosurgery.

2. Description of the Related Art

In general, a spine forms a pillar of the body, and an upper portion thereof is a portion forming a backbone of a human body that connects an upper skull and a lower pelvis. The spine includes 7 cervical vertebrae, 12 thoracic vertebrae, 5 lumbar vertebrae, 5 sacral vertebrae, and 3 to 5 coccyges from the top. In such a spine, symptoms such as an intervertebral disc disease and lumbar herniated intervertebral disc are likely to occur by prolonged or excessive use. In general, patients having spinal disorders such as spinal fracture and dislocation are subjected to treatment and correction by fixing the respective vertebrae so as not to be moved relative to each other. For this, a spinal fixation device has been widely used for fixing the vertebrae during fusion in the art.

Such a spinal plate generally refers to an implantation plate used for treatment of the spinal disorders. The spinal implant is used for spinal fusion in which a fusion cage of an artificial implant is inserted between vertebrae from which a damaged intervertebral disk is removed due to various spinal disorders, thus to restore and maintain an interval between the vertebrae. In the conventional case, the fusion cage inserted between the vertebrae is used simultaneously with bone screws and a rod applied simultaneously to the back of the vertebral body, or is used in such a manner in which the cage is coupled and fixed by a plate and connection bolts screwed to the vertebrae, or the cage itself is equipped with bone screw holes that can be installed the bone screws to directly fix the cage to the vertebrae.

However, since spin shapes are very diverse depending on conditions of the patients during the surgery, a case in which a doctor needs to use the spinal plate by modifying the shape thereof for each situation occurs. However, it is not easy to accurately modify the shape of the spinal plate according to the various spin shapes of the patients. Therefore, when actually performing the surgery, there are problems that the spinal plate does not adhere to the vertebrae but is detached or somewhat incompletely attached, thereby side effects occur or the surgery has to be performed again.

In addition, the patients prefer minimally invasive spine (MIS) surgery because of its potential benefits: less blood loss from surgery, reduced risk of muscle damage, reduced risk of infection and postoperative pain, faster recovery time, better cosmetic results because of relatively smaller skin incisions, etc. In order to perform MIS surgery, it is crucial that the doctors should be able to gain access to the spinal area by making as smaller skin incisions as possible and insert the spinal plate through these small skin incisions. In other words, the spinal plate, whose shape can be easily modified depending on conditions of the patients during the surgery and which can be inserted through patients' small skin incisions, is required for successful MIS surgery.

PRIOR ART DOCUMENT

Patent Document (Patent Document 1) U.S. Patent Application Publication No. US 2018-0235671A
(Patent Document 2) U.S. Patent Application Publication No. US 2013-0060283A

SUMMARY OF THE INVENTION

An object of the present invention is to provide a spinal plate in which a rotation device and a locking device are installed so as to be used by fixing any one or more of longitudinal ends of the plate with being rotated at any angle, thereby allowing a doctor to use the spinal plate by modifying a shape thereof to the shape desired by the doctor during a surgery, and to perform the surgery by coping with various spin shapes of patients.

In order to achieve the above object, according to an aspect of the present invention, there is provided a spinal plate including: a central body; and a pair of end bodies which are disposed on both sides of the central body and have one or more fixing screw holes in which fixing screws to be inserted into vertebrae are received, wherein at least one of the pair of end bodies includes a rotation device configured to fix the end body to the central body in a selectively rotatable manner, and a locking device configured to maintain the rotation device in an unlocked state or a locked state.

Herein, the central body may include one or more fixing screw holes formed therein, in which fixing screws to be inserted into vertebrae are received.

In addition, the rotation device may include: central pin joints formed at both ends of the central body; end pin joints formed at ends of the end bodies; and rotation pins which are inserted into the central pin joints and the end pin joints in a penetration manner.

Further, the locking device may include: central locking parts formed in the central pin joints so as to be located outside the rotation pin; end locking part formed in the end pin joint so as to be located outside the rotation pin; and a locking tube which is inserted into the central pin joints and the end pin joint outside of the rotation pin to be fastened to the end locking part and the central locking parts so as to prevent rotations thereof.

Further, the locking tube may include: a tube locking part which is formed on an outer circumference thereof to come into contact with the end locking part and the central locking part, and is configured to fix a relative position between the end locking part and the central locking part; and a knob formed at one end thereof.

Further, the central locking part may be a central serration formed in the central pin joint along an inner circumference thereof, the end locking part may be an end serration formed in the end pin joint along an inner circumference thereof, and the tube locking part may be a tube serration formed on an outer circumference of the locking tube to come into contact with both the central serration and the end serration.

Further, the central locking part may be a plurality of locking grooves or locking protrusions formed on an inner circumference of the central pin joint in a circumferential direction thereof, the end locking part may be a plurality of locking grooves or locking protrusions formed on an inner circumference of the end pin joint in a circumferential direction thereof, and the tube locking part may be a key groove or a key protrusion which is formed on the outer circumference of the locking tube in an elongated form so as to fix the relative position between the central locking part and the end locking part.

Further, the knob may be formed in a polygonal shape, or may have protrusions or grooves formed on an outer circumference thereof, so as to facilitate gripping.

Further, the knob may have a device coupling part formed on an inner surface thereof for coupling with the device.

Further, the device coupling part may be a female thread formed on the inner surface of the knob.

Further, the device coupling part may be coupling recesses or coupling protrusions formed on the inner surface of the knob.

Further, the rotation device may include one and/or two end pin joint(s) and two and/or one central pin joint(s), such that the one end/central pin joint is inserted between the two central/end pin joints.

Further, a rotation pin support seat may be formed only in one end/central pin joint of the two central/end pin joints.

Further, the rotation device may include rotational locking units which are rotatably disposed in the central body, and come into contact with an outer surface of the end pin joint to prevent a rotation of the end body.

Furthermore, the central body may include: rotational locking unit seats formed therein, into which the rotational locking units are inserted; and openings formed on one side of each rotational locking unit seat to expose a side face of the rotational locking unit toward the end pin joint.

Furthermore, the rotational locking unit may include: a rotational protrusion inserted into the rotational protrusion seat formed in the rotational locking unit seat; a rotational locking unit body formed integrally with the rotational protrusion; a contact surface formed on one portion of an outer surface of the rotational locking unit body to come into contact with the end pin joint; and a non-contact surface which is formed on the other portion of the outer surface of the rotational locking unit body and continuously forms the contact surface without contacting the end pin joint.

Furthermore, the spinal plate may include: a central body; a pair of rotation portions, the pair of rotation portions being disposed on both sides in a longitudinal direction of the central body. Each of the pair of rotation portions comprises a bone screw for being inserted into vertebrae.

Furthermore, the central body may include: a central hole; and two rotational locking units. The two rotational locking units are configured to be released or fastened.

Furthermore, each of the pair of rotation portions comprises a rotation connection portion, and the central body comprises a rotation support portion.

Furthermore, the spinal plate may include rotation pins. The rotation pins are configured to connect the central body with the pair of rotation portions and are configured to enable the pair of rotation portions to rotate with respect to the central body at any angle.

Furthermore, each of the pair of rotation portions is configured to rotate with respect to the central body counterclockwise for a rotation portion disposed on a right side of the central body and clockwise for a rotation portion disposed on a left side of the central body. An angle between each of the pair of rotation portions and the central body is up to 90 degree with respect to the longitudinal direction of the central body.

Furthermore, the angle between each of the pair of rotation portions and the central body is larger than 90 degree with respect to the longitudinal direction of the central body.

Furthermore, each of the pair of rotation portions comprises a rotation connection portion, and the central body comprises a rotation support portion. A rotation of each of the pair of rotation portions is restricted by an upper portion of the rotation support portion as the rotation connection portion rotates with each of the pair of rotation portions.

Furthermore, each of the pair of rotation portions is configured to rotate with respect to the central body clockwise for a rotation portion disposed on a right side of the central body and counterclockwise for a rotation portion disposed on a left side of the central body. An angle between each of the pair of rotation portions and the central body is less than 45 degree with respect to the longitudinal direction of the central body.

Furthermore, a rotation of each of the pair of rotation portions is restricted by a rotational angle control portion formed between a bottom portion of the central body and a bottom portion of each of the pair of rotation portions.

Furthermore, each of the pair of rotation portions comprises a spike screw.

Furthermore, the spike screw comprises a head portion and a body portion, and the head portion and the body portion have different threads.

Furthermore, a pitch of the thread in the head portion is smaller than a pitch of the thread in the body portion, thereby enabling self-locking while pulling the vertebrae to the spinal plate.

Furthermore, a washer is put on the bone screw on a washer support part on each of the pair of rotation portions.

Furthermore, the spinal plate is designed such that the washer is configured to rotate with respect to each of the pair of rotation portions and a head of the bone screw is configured to rotate with respect to the washer.

Furthermore, the angle between each of the pair of rotation portions and the central body may be up to 20 degree with respect to the longitudinal direction of the central body.

According to the present invention, the rotation device and the locking device may be installed so as to be used by fixing any one or more of longitudinal ends of the plate with being rotated at any angle, thereby allowing a doctor to modify a shape of the spinal plate to the shape desired by the doctor, and to perform the surgery by coping with various spin shapes of the patients.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a perspective view illustrating a spinal plate according to Embodiment 1 of the present invention;

FIG. 2 is a perspective view illustrating a central body of the spinal plate according to Embodiment 1 of the present invention;

FIG. 3 is a perspective view illustrating an end body of the spinal plate according to Embodiment 1 of the present invention;

FIG. 4 is a perspective view illustrating a rotation pin of the spinal plate according to Embodiment 1 of the present invention;

FIG. 5 is a perspective view illustrating a locking tube of the spinal plate according to Embodiment 1 of the present invention;

FIG. 6 is a perspective view illustrating a state in which the locking tube is released in the spinal plate according to Embodiment 1 of the present invention;

FIG. 7 is a perspective view illustrating a state in which the locking tube is fastened in the spinal plate according to Embodiment 1 of the present invention;

FIG. 8 is a perspective view illustrating a state in which the end bodies are rotated with respect to the central body and then the locking tubes are fastened to lock the end bodies of the spinal plate according to Embodiment 1 of the present invention;

FIG. 9 is a perspective view illustrating a state in which the end bodies are rotated with respect to the central body and then the locking tubes are released to unlock the end bodies of the spinal plate according to Embodiment 1 of the present invention;

FIG. 10 is a perspective view illustrating a spinal plate according to Embodiment 2 of the present invention with being unlocked;

FIG. 11 is a perspective view illustrating a central body of the spinal plate according to Embodiment 2 of the present invention;

FIG. 12 is a perspective view illustrating an end body of the spinal plate according to Embodiment 2 of the present invention;

FIG. 13 is a perspective view illustrating a rotational locking unit of the spinal plate according to Embodiment 2 of the present invention;

FIG. 14 is a perspective view illustrating a rotation pin of the spinal plate according to Embodiment 2 of the present invention;

FIG. 15 is a partially enlarged perspective view of the spinal plate according to Embodiment 2 of the present invention with the rotational locking units being released;

FIG. 16 is a partially enlarged perspective view of the spinal plate according to Embodiment 2 of the present invention with the rotational locking units being fastened;

FIG. 17 is a perspective view illustrating the spinal plate according to Embodiment 2 of the present invention with being locked;

FIG. 18 is a perspective view illustrating a spinal plate according to Embodiment 3 of the present invention;

FIG. 19 is a top view illustrating a spinal plate according to Embodiment 3 of the present invention;

FIG. 20 is a bottom view illustrating a spinal plate according to Embodiment 3 of the present invention;

FIG. 21 is a perspective view of separate components in a spinal plate according to Embodiment 3 of the present invention;

FIG. 22 is a partially enlarged perspective view of the spinal plate according to Embodiment 3 of the present invention with a washer put on a bone screw on a washer support part on each of the pair of rotation portions; and FIG. 23 is a partially enlarged perspective view of the spinal plate according to Embodiment 3 of the present invention with a rotational angle control portion formed between a bottom portion of the central body and a bottom portion of each of the pair of rotation portions.

DETAILED DESCRIPTION OF THE INVENTION

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

A spinal plate 100 according to Embodiment 1 of the present invention will be described with reference to FIGS. 1 to 9. FIG. 1 is a perspective view illustrating the spinal plate 100 according to Embodiment 1 of the present invention. As illustrated in FIG. 1, the spinal plate 100 basically includes: a central body 102; and a pair of end bodies 104 and 106 which are disposed on both sides in a longitudinal direction of the central body 102 and have one or more fixing screw holes 110 formed therein, in which fixing screws to be inserted into vertebrae are received, wherein at least one of the pair of end bodies 104 and 106 includes a rotation device for fixing the end body to the central body 102 in a selectively rotatable manner, and a locking device for maintaining the rotation device in an unlocked state or a locked state.

The spinal plate 100 may be made of a known material such as titanium, a Co—Cr alloy, or the like, but it is not limited thereto.

The fixing screw hole 110 may include a screw support part 108 so as to support a head of the received fixing screw (not illustrated). When using the spinal plate 100 between a pair of adjacent vertebral bodies, it is sufficient for the fixing screw holes 110 formed in the end bodies 104 and 106 on both sides, but when using the spinal plate for three or more vertebral bodies, it is possible to further from one or more fixing screw holes for receiving the fixing screws to be inserted into the vertebrae in the central body 102.

FIG. 2 is a perspective view illustrating the central body of the spinal plate 100 according to Embodiment 1 of the present invention. As illustrated in FIG. 2, the central body 102 may include: central pin joints 118 and 124 formed at both ends thereof; and central locking parts formed in the central pin joints 118 and 124 and a window 128 formed in a central portion thereof.

FIG. 3 is a perspective view illustrating the end body of the spinal plate according to Embodiment 1 of the present invention. As illustrated in FIG. 3, the end bodies 104 and 106 may include one or more fixing screw holes 110 which are disposed on both sides in the longitudinal direction of the central body 102, and receive the fixing screws to be inserted into the vertebrae. In addition, the end bodies 104 and 106 may include an end pin joint 112 formed at an end thereof and an end locking part formed in the end pin joint 112.

The end locking part may be an end serration 114 formed on the inner circumference of the end pin joint 112, and may be a plurality of locking grooves or locking protrusions (not illustrated) formed on the inner circumference of the end pin joint 112 in a circumferential direction thereof.

The rotation device may include: the central pin joints 118 and 124 formed at the both ends of the central body 102; the end pin joints 112 formed at the ends of the end bodies 104 and 106; and rotation pins 130 which are inserted into the central pin joints 118 and 124 and the end pin joints 112 in a penetration manner.

In Embodiment 1, the rotation device may include one end pin joint 112 and two central pin joints 118 and 124 spaced apart from each other, and the end pin joint 112 is inserted between the two central pin joints 118 and 124. On the other hand, in one variant, the rotation device may include two end pin joints and one central pin joint, such that the central pin joint is inserted between the two end pin joints. Additionally, the rotation device may also include one central pin joint and one end pin joint, and various variants are possible other than the above-described configurations.

The locking device may include: the central locking parts formed in the central pin joints 118 and 124 so as to be located outside the rotation pin 130; the end locking part formed in the end pin joint 112 so as to be located outside the rotation pin 130; and a locking tube 140 which is inserted into the central pin joints 118 and 124 and the end pin joint 112 outside of the rotation pin 130 to be fastened to the end locking part and the central locking parts so as to prevent rotations thereof.

The central locking parts may be central serrations 120 and 126 formed on an inner circumference of the central pin joints 118 and 124. As pitches of the central serrations 120 and 126 are decreased, various angles may be implemented, but on the other hand, the pitch is reduced to cause a deterioration in mechanical performance. Therefore, it is important to determine the pitch of the central serrations 120 and 126 so that the stability can be secured through a performance test, as well as a range of angle change can be small.

In addition, the central locking parts may be a plurality of locking grooves or locking protrusions (not illustrated) formed on the inner circumference of the central pin joints 118 and 124 in a circumferential direction thereof.

The window 128 may serve as a view port for checking a vertebral surface that comes into contact with the spinal plate during the surgery, and may also be utilized as an application for coupling a device through the window 128.

FIG. 4 is a perspective view illustrating the rotation pin 130 of the spinal plate 100 according to Embodiment 1 of the present invention. As illustrated in FIG. 4, the rotation pin 130 may include a rotation pin central portion 132 and rotation pin end portions 134 and 136, and pass through the central pin joints 118 and 124 and the end serration 114 to be inserted into the central locking parts and the end locking part. A length of the rotation pin 130 may be equal to or shorter than a distance between the outermost ends of two central body joints 118 and 124 so as not to be exposed to an outside of the two central body joints 118 and 124.

In addition, the end pin joint 112 may have a rotation pin support seat 116 formed therein, on which the rotation pin 130 is rotatably seated while being in contact therewith. By forming the rotation pin support seat 116 in the end pin joint 112, it is possible to stably support the rotation pin 130 so as to prevent it from being removed outward. Further, to this end, a cross section of a portion of the rotation pin 130 that comes into contact with the rotation pin support seat 116 may be formed to be smaller than those of outer portions from the portion in the longitudinal direction.

FIG. 5 is a perspective view illustrating the locking tube 140 of the spinal plate 100 according to Embodiment 1 of the present invention. As illustrated in FIG. 5, the locking tube 140 may include a tube locking part which is formed on an outer circumference thereof to come into contact with the end locking part and the central locking part, and is configured to fix a relative position between the end locking part and the central locking part, and a knob 144 formed at one end thereof.

The tube locking part may be a tube serration 142 formed on an outer circumference of the locking tube 140 having teeth 143 to come into contact with both the central serrations 120 and 126 and the end serration 114.

In addition, the tube locking part may be a key groove or a key protrusion (not illustrated) which is formed on the outer circumference of the locking tube 140 in an elongated form so as to fix the relative position between the central locking part and the end locking part. That is, two or more key grooves or key protrusions are formed on the outer circumference of the locking tube 140 as the tube locking part, so as to be inserted into a plurality of protrusions or grooves which are radially formed on inner circumferences of the central pin joints 118 and 124 as the central locking part and the end pin joint 112 as the end locking part at any angle corresponding to the key groove or key protrusion of the tube locking part.

The shapes of the tube locking part, the central locking part, and the end locking part are not limited to those described above, and various modifications are possible.

The knob 144 may be formed in a polygonal shape, or may have protrusions or grooves formed on the outer circumference thereof, thereby facilitating gripping. The knob 144 may serve as a grip to facilitate insertion when inserting the locking tube 140 into the central locking part and the end locking part.

In addition, the knob 144 may have a device coupling part 146 formed on an inner surface thereof for coupling with the device, and the device coupling part 146 may be a female thread, coupling recesses or coupling protrusions formed on the inner surface of the knob 144. In the present invention, by forming the female thread, coupling recesses or coupling protrusions in the knob 144 as the device coupling part 146, even after the locking tube 140 is fastened to the central locking part and the end locking part to be the locked state, the locking tube 140 is released by coupling a device (not illustrated) to the device coupling part 146 formed in the knob 144 to return it to the unlocked state again. At this time, in a state in which the rotation pin 130 is pressed to one side, the device (not illustrated) is coupled to the device coupling part 146, or the length of the rotation pin 130 is formed to be smaller than an entire length of the central pin joint 118 and 124 and the end pin joint 112.

FIG. 6 is a perspective view illustrating a state in which the locking tube 140 is released in the spinal plate 100 according to Embodiment 1 of the present invention, and FIG. 7 is a perspective view illustrating a state in which the locking tube 140 is fastened in the spinal plate 100 according to Embodiment 1 of the present invention. As illustrated in FIGS. 6 and 7, the rotation pin 130 is inserted through the central pin joints 118 and 124 and the end pin joint 112, and may be stably inserted due to the rotation pin support seat 116 formed in the end pin joint 112.

In the unlocked state which is a state before the locking tube 140 is completely fastened to the central locking part and the end locking part as illustrated in FIG. 6, it is possible to adjust so that the end bodies 104 and 106 are positioned at a desired angle with respect to the central body 102. Further, in the locked state which is a state in which the locking tube 140 is completely fastened to the central locking part and the end locking part as illustrated in FIG. 7, rotations of the end bodies 104 and 106 with respect to the central body 102 are prevented to be a fixed state.

FIG. 8 is a perspective view illustrating a state in which the end bodies 104 and 106 are rotated with respect to the central body 102 and then the locking tubes 140 are fastened to lock the end bodies 104 and 106 of the spinal plate 100 according to Embodiment 1 of the present invention, and FIG. 9 is a perspective view illustrating a state in which the end bodies 104 and 106 are rotated with respect to the central body 102 and then the locking tubes 140 are released to unlock the end bodies 104 and 106 of the spinal plate 100 according to Embodiment 1 of the present invention. As illustrated in FIGS. 8 and 9, according to the present invention, the end bodies 104 and 106 may be adjusted to be positioned at a desired angle with respect to the central body 102. Even after the locked state as illustrated in FIG. 8, the locking tube 140 may be released by the device coupling part 146 formed in the knob 144 of the locking tube 140 to return it to the unlocked state again as illustrated in FIG. 9.

Next, a spinal plate 200 according to Embodiment 2 of the present invention will be described with reference to the FIGS. 10 to 17. FIG. 10 is a perspective view illustrating the spinal plate 200 according to Embodiment 2 of the present invention. As illustrated in FIG. 10, the spinal plate 200 basically includes: a central body 202; and a pair of end bodies 204 and 206 which are disposed on both sides in a longitudinal direction of the central body 202 and have one or more fixing screw holes 210 in which the fixing screws to be inserted into vertebrae are received, wherein at least one of the pair of end bodies 204 and 206 includes a rotation device for fixing the end body to the central body 202 in a selectively rotatable manner, and a locking device for maintaining the rotation device in an unlocked state or a locked state, which are the same as Embodiment 1.

The spinal plate 200 may be made of a known material such as titanium, Co—Cr alloy, but it is not limited thereto.

The fixing screw hole 210 may include a screw support part 208 so as to support a head of the received fixing screw (not illustrated). When using the spinal plate 200 between a pair of adjacent vertebral bodies, it is sufficient for the fixing screw holes 210 formed in the end bodies 204 and 206 on both sides, but when using the spinal plate for three or more vertebral bodies, it is possible to further from one or more fixing screw holes for receiving the fixing screws to be inserted into the vertebrae in the central body 202.

FIG. 11 is a perspective view illustrating the central body 202 of the spinal plate 200 according to Embodiment 2 of the present invention. As illustrated in FIG. 11, the central body 202 may include: central pin joints 218 and 224 formed at both ends thereof; and central pin holes 220 and 226 formed in the central pin joints 218 and 224. Further, a window 228 may be additionally formed in the central body 202.

FIG. 12 is a perspective view illustrating the end body of the spinal plate according to Embodiment 2 of the present invention. As illustrated in FIG. 12, the end bodies 204 and 206 may include one or more fixing screw holes 210 which are disposed on both sides in the longitudinal direction of the central body 202, and receive the fixing screws to be inserted into the vertebrae. In addition, the end bodies 204 and 206 may include an end pin joint 212 formed at an end thereof and an end pin hole 214 formed in the end pin joint 212.

The rotation device may include: the central pin joint 218 and 224 formed at the both ends of the central body 202; the end pin joints 212 formed at the ends of the end bodies 204 and 206; and rotation pins 230 which are inserted into the central pin joints 218 and 224 and the end pin joints 212 in a penetration manner.

In Embodiment 2, the rotation device may include one end pin joint 212 and two central pin joints 218 and 224 spaced apart from each other, and the end pin joint 212 is inserted between the two central pin joints 218 and 224. On the other hand, in one variant, the rotation device may include two end pin joints and one central pin joint, such that the central pin joint is inserted between the two end pin joints. Additionally, the rotation device may also include one central pin joint and one end pin joint, and various variants are possible other than the above-described configurations.

The spinal plate 200 of Embodiment 2 is characterized in that the rotation device includes rotational locking units 240 which are rotatably disposed in the central body 202, and come into contact with an outer surface of the end pin joint 212 to prevent rotations of the end bodies 204 and 206.

To this end, the central body 202 may include: rotational locking unit seats 252 formed therein, into which the rotational locking units 240 are inserted; and openings 254 formed on one side of each rotational locking unit seat 252 to expose a side face of the rotational locking unit 240 toward the end pin joint 212. In addition, a rotational protrusion seat 256 may be formed in the rotational locking unit seat 252 to rotatably support the rotational locking unit 240.

In addition, as illustrated in FIG. 13, the rotational locking unit 240 may include: a rotational protrusion 248 inserted into the rotational protrusion seat 256 formed in the rotational locking unit seat 252; a rotational locking unit body 242 formed integrally with the rotational protrusion 248; a contact surface 244 formed on one portion of an outer surface of the rotational locking unit body 242 to come into contact with the end pin joint; and a non-contact surface 246 which is formed on the other portion of the outer surface of the rotational locking unit body 242 and continuously forms the contact surface 244 without contacting the end pin joint 212. Further, the rotational locking unit body 242 may have a device groove 250 formed on an upper side thereof, into which a device is inserted. On the other hand, a device protrusion may be formed on the rotational locking unit body 242 to be inserted the device.

The rotational protrusion seat 256 and the rotational protrusion 248 are coupled to each other in such a way that: the rotational protrusion 248 is inserted into a rotation ring, an annular ring, or an annular groove formed in the rotational protrusion seat 256; the rotational protrusion 248 has a structure formed on the outer circumference thereof corresponding to the rotational protrusion seat 256 to be tightly fitted with each other; or an end of the rotational protrusion 248 penetrates a hole formed in the rotational protrusion seat 256 and fixed thereto by using known techniques such as riveting or inserting a fixing bolt. The rotational locking unit body 242 may have a bolt shape as a whole, and the device groove 250 formed at the upper center thereof may have a known shape such as a hexagonal or star shape. Further, it is also possible to form a hexagonal or star-shaped protrusion in the rotational locking unit body 242 in place of the device groove 250. The outer circumference of the rotational locking unit body 242 has a cylindrical shape as a whole, and a cut-out portion thereof on one side corresponds to the non-contact surface 246, and the remaining portion thereof, which is not cut-out, corresponds to the contact surface 244. A center angle of the non-contact surface 246 and the contact surface 244 can be selected by a designer as necessary. However, in Embodiment 2, when the non-contact surface 246 is positioned at the opening 254, a width of the non-contact surface 246 is substantially equal to that of the opening 254. In addition, a cut-out thickness of the non-contact surface 246 is set so as to have a level coinciding with surrounding surfaces when the non-contact surface 246 is located at the opening 254.

The window 228 is formed in the central body 202 to serve as a view port for checking a vertebral surface that comes into contact with the spinal plate during the surgery, and may also be utilized as an application for coupling a device through the window 228.

FIG. 14 is a perspective view illustrating the rotation pin 230 of the spinal plate 200 according to Embodiment 2 of the present invention. As illustrated in FIG. 14, the rotation pin 230 may include a rotation pin central portion 232 and the rotation pin end portions 234 and 236, and pass through the central pin joints 218 and 224 and the end locking part to be inserted into the central pin holes 220 and 226 and the end pin hole 214. A length of the rotation pin 230 may be equal to or shorter than a distance between the outermost ends of two central pin joints 218 and 224 so as not to be exposed to the outside of the two central pin joints 218 and 224.

In addition, the end pin joint 212 may have a rotation pin support seat (not illustrated) formed therein, on which the rotation pin 230 is rotatably seated while being in contact therewith, which is the same as Embodiment 1. By forming the rotation pin support seat in the end pin joint 212, it is possible to stably support the rotation pin 230 so as to prevent it from being removed outward. Further, to this end, a cross section of a portion of the rotation pin 230 that comes into contact with the rotation pin support seat may be formed to be smaller than those of the portions outside the portion. In addition, the rotation pin support seat may be formed in any one of the central pin joints 218 and 224. Additionally, it is also possible to form the rotation pin support seats in both the central pin joints 218 and 224 and the end pin joint 212.

Hereinafter, an operation of the spinal plate 200 will be described with reference to FIGS. 15 to 17.

As illustrated in FIG. 15, when the non-contact surface 246 of the rotational locking unit 240 is positioned at the opening 254 of the central body 202, it is referred to an open state. In this case, since the non-contact surface 246 of the rotational locking unit 240 does not contact with the surface of the end pin joint 212, the end bodies 204 and 206 can move freely with respect to the central body 202.

Thus, as illustrated in FIG. 16, a user rotates the end bodies 204 and 206 with respect to the central body 202 to make the spinal plate be a desired angle, then rotates the rotational locking unit 240 so that the contact surface 244 protrudes through the opening 254. In Embodiment 2 of the present invention, since four rotational locking units 240 are disposed by two on each side, the above-described operations are repeated four times.

As a result, as illustrated in FIG. 17, the spinal plate 200 can be fixed with the end bodies 204 and 206 being angularly rotated with respect to the central body 202 at any angle.

Next, a spinal plate 300 according to Embodiment 3 of the present invention will be described with reference to the FIGS. 18-23. FIG. 18 is a perspective view illustrating the spinal plate 300 according to Embodiment 3 of the present invention. FIG. 19 is a top view illustrating a spinal plate according to Embodiment 3 of the present invention. FIG. 20 is a bottom view illustrating a spinal plate according to Embodiment 3 of the present invention. FIG. 21 is a perspective view of separate components in a spinal plate according to Embodiment 3 of the present invention.

As illustrated in FIG. 18, the spinal plate 300 basically includes: a central body 302; and a pair of rotation portions 312 which are disposed on both sides in a longitudinal direction of the central body 302 and each of the pair of rotation portions 312 has bone screw 308. These bone screws 308 are inserted into vertebrae. The spinal plate 300 further includes: spike screw 306 in each of the pair of rotation portions 312. The central body 302 includes a center hole 318 and two rotational locking units 340. These rotational locking units 340 can be released and/or fastened, as shown in FIGS. 15 and 16. Each of the pair of rotation portions 312 include a rotation connection portion 316, and the central body includes a rotation support portion 314. Rotation pins 330 are used to connect the central body 302 with the pair of rotation portions 312 disposed on both sides in a longitudinal direction of the central body 302 and enable the pair of rotation portions 312 to rotate with respect to the central body 302. The rotation pins 330 are the same as Embodiments 1 and 2.

As illustrated in FIG. 18, the spinal plate 300 according to Embodiment 3 of the present invention is specifically targeted for MIS surgery.

The pair of rotation portions 312, disposed on both sides in a longitudinal direction of the central body 302, are rotated with respect to the central body 302 at any angle, thereby allowing a doctor to use the spinal plate by modifying a shape thereof to the shape desired by the doctor during MIS surgery, and to perform the surgery by coping with various spin shapes of patients. In particular, each of the pair of rotation portions 312 can be rotated with respect to the central body 302 counterclockwise (for a rotation portion 312 disposed on the right side of the central body 302) or clockwise (for a rotation portion 312 disposed on the left side of the central body 302) so that an angle between each of the pair of rotation portions 312 and the central body 302 is up to 90 degree with respect to a longitudinal direction of the central body 302 ("twelve o'clock"). This angle between each of the pair of rotation portions 312 and the central body 302 can be larger than 90 degree. The rotation of each of the pair of rotation portions 312 is restricted by an upper portion of the rotation support portion 314 (surface on which two rotational locking units 340 are positioned) as the rotation connection portion 316 rotates with each of the pair of rotation portions 312.

In addition, each of the pair of rotation portions 312 can be rotated with respect to the central body 302 clockwise (for a rotation portion 312 disposed on the right side of the central body 302) or counterclockwise (for a rotation portion 312 disposed on the left side of the central body 302) so that an angle between each of the pair of rotation portions 312 and the central body 302 is less than 45 degree (preferably, up to 20 degree) with respect to a longitudinal direction of the central body 302 ("four o'clock" or "eight o'clock"). The reason for limiting up to 45 degree (preferably, up to 20 degree) is that the spinal plate is to be supported by the compressive force applied in a direction that an upper and a lower vertebrae are close to each other (the weight exerted by the human body). If this angle is greater than 45 degree, the rotation part 312 would fail to properly transmit the compression to the body. This rotation is restricted by a rotational angle control portion 310 formed between a bottom portion 322 of the central body 302 and a bottom portion 320 of each of the pair of rotation portions 312. This means that there are two rotational angle control portions 310 formed between two opposite bottom end portions 322 of the central body 302 in a longitudinal direction of the central body 302 (bottom left end and bottom right end sides of the central body 302) and two bottom portions 320 of each of the pair of rotation portions 312. As illustrated in FIG. 23, there is a gap between a bottom portion 322 of the central body 302 and a bottom portion 320 of each of the pair of rotation portions 312. In addition, two opposite bottom end portions 322 of the central body 302 are designed such that they are slightly indented inward toward a center of the central body 302 in the longitudinal direction of the central body 302. However, the design of two opposite bottom end portions 322 of the central body 302 is not limited as illustrated in FIG. 23.

Specifically, when making a surgical path for surgery, and inserting the spinal plate 300 to the surgical path, each of the pair of rotation portions 312 is folded upward with respect to the spinal plate 300. When the spinal plate 300 is placed on the surgical site (precisely, positioned to span the upper and lower vertebrae around the disk), each of the pair of rotation portion 312 is rotated to contact the vertebrae. At this point, the end of the vertebrae is slightly larger in diameter than other parts of the vertebrae. Therefore, with the spinal plate 300 in contact with the vertebrae, each of the pair of rotation portion 312 rotates more than the spinal plate's longitudinal plane, which rotates as if it is surrounding the end of the vertebrae. At this point, the bone screw 308 is inserted. Due to the rotation of the each of the pair of rotation part 312, the bone screw 308 is inserted inside the spine (e.g., in the disc direction) with respect to a perpendicular direction of the spinal plate 300. Therefore, insertion directions of the bone screw 308 can be adjusted to a horizontal or an upward direction of the spine using the washer 304. The insertion of the bone screw 308 can then be fixed at any angle with friction between the washer 304 and the head of the bone screw 308, the washer 304 and the spinal plate 300, as discussed above. Furthermore, the washer 304 can enlarge the insertion directions of the bone screw 308 both vertically and horizontally.

Furthermore, the spinal plate 300 according to Embodiment 3 of the present invention includes spike screw 306 on each of the pair of rotation portions 312. In the conventional case, spike or teeth is used and formed integrally with the spinal plate. However, this spike or teeth does not provide a robust capability to securely adhere the spinal plate to the vertebrae. Therefore, the present invention applies the spike screw 306 on each of the pair of rotation portions 312. This spike screw 306 includes a head portion 326 and a body portion 328, and the head portion 326 and the body portion 328 have different threads. The spike screw 306 is designed such that a pitch of the thread in the head portion 326 is smaller than a pitch of the thread in the body portion 328, thereby enabling self-locking while pulling the vertebrae to the spinal plate. The head portion 326 of the spike screw 306 is screwed with a spike screw support part 334 of the rotation portion 312.

As illustrated in FIG. 22, a washer 304 is put on the bone screw 308 on a washer support part 332 on each of the pair of rotation portions 312. The washer 304 is assembled with the spinal plate 300 and pressed fitted in the manufacturing facility. During the manufacturing process, a top portion 324 of the washer 304 is inserted inside the washer support part 332 after deflation. The top portion 324 of the washer 304 is enlarged inside the washer support part 332 after the insertion. During the surgery, the bone screw 308 is inserted into the washer 304 to secure the spinal plate 300 to the vertebral body. Therefore, a head of the bone screw 308 presses down on the washer 304, and the washer 304 presses down on the washer support part 332 of t20he rotation portion 312, thereby creating friction. The design of the washer 304 is not limited as illustrated in FIG. 21. The washer 304 surrounds a head of the bone screw 308 and is designed such that the washer 304 can be easily put on the circular (oval or round) head of the bone screw 308. In order to increase insertion angles of the bone screw 308, the spinal plate 300 is designed such that the washer 304 rotates with respect to each of the pair of rotation portions 312 and a head of the bone screw 308 rotates with respect to the washer 304. By having large insertion angles of the bone screw 308, when both sides of rotation portion 312 are rotated downward than the body, inserting the bone screw 308 would cause the bone screw 308 to face inward. In order to solve this problem, insertion angles of the bone screw 308 is designed such that these angles can be adjusted arbitrarily. Inserting and securing the bone screw 308 would push the washer 304, which would tighten and hold the head of the bone screw 308 by friction.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

According to the present invention, it is possible to use the spinal plate by modifying the shape thereof in the shape desired by the doctor during the surgery, thereby developing a spinal plate that can cope with the various spin shapes of the patients.

In addition, the shape of the spinal plate may be deformed at various angles with a single plate, it is possible to reduce the burden of preparing the plates for each operation during the surgery, thereby greatly reducing product costs from the manufacturer's point of view.

DESCRIPTION OF REFERENCE NUMERALS 100, 200, 300: Spinal plate
102, 202, 302: Central body
104, 106, 204, 206: End body
108, 208: Screw support part
110, 210: Fixing screw hole
112, 212: End pin joint
114: End serration
118, 124, 218, 224: Central pin joint
116: Rotation pin support seat
120, 126: Central serration
128, 228: Window
130, 230, 330: Rotation pin
132, 232: Rotation pin central portion
134, 136, 234, 236: Rotation pin end portion
140: Locking tube
142: Tube serration
143: Teeth
144: Knob
146: Device coupling part
214: End pin hole
220, 226: Central pin hole
240, 340: Rotational locking unit
242: Rotational locking unit body
244: Contact surface
246: Non-contact surface
248: Rotational protrusion
250: Device groove
252: Rotational locking unit seat
254: Opening
256: Rotational protrusion seat
304: Washer
306: Spike screw
308: Bone screw
310: Rotational angle control portion
312: Rotation portion
314: Rotation support portion
316: Rotation connection portion 318: Center hole
320: Bottom portion of rotation portion
322: Bottom portion of central body
324: Top portion of washer
326: Head portion of spike screw
328: Body portion of spike screw
332: Washer support part
334: Spike screw support part

What is claimed is:

1. A spinal plate comprising:
   a central body;
   a pair of rotation portions, the pair of rotation portions being disposed on both sides of the central body in a width direction of the central body with respect to a longitudinal direction of the central body; and
   rotation pins,
   wherein each of the pair of rotation portions comprises a bone screw for being inserted into vertebrae,
   wherein the rotation pins are configured to connect the central body with the pair of rotation portions and are configured to enable the pair of rotation portions to rotate with respect to the central body at any angle,
   wherein each of the pair of rotation portions is configured to rotate with respect to the central body clockwise for a rotation portion disposed on a right side of the central body and counterclockwise for a rotation portion disposed on a left side of the central body, and
   wherein a first angle between each of the pair of rotation portions and the central body is less than 45 degree with respect to the longitudinal direction of the central body.

2. The spinal plate according to claim 1, wherein the central body comprises:
   a central hole; and
   two rotational locking units,
   wherein the two rotational locking units are configured to be released or fastened.

3. The spinal plate according to claim 1, wherein each of the pair of rotation portions comprises a rotation connection portion, and the central body comprises a rotation support portion.

4. The spinal plate according to claim 1, wherein each of the pair of rotation portions is configured to rotate with respect to the central body counterclockwise for a rotation portion disposed on a right side of the central body and clockwise for a rotation portion disposed on a left side of the central body, and
   wherein a second angle between each of the pair of rotation portions and the central body is up to 90 degree with respect to the longitudinal direction of the central body.

5. The spinal plate according to claim 1, wherein each of the pair of rotation portions is configured to rotate with respect to the central body counterclockwise for a rotation portion disposed on a right side of the central body and clockwise for a rotation portion disposed on a left side of the central body, and
   wherein a second angle between each of the pair of rotation portions and the central body is larger than 90 degree with respect to the longitudinal direction of the central body.

6. The spinal plate according to claim 1, wherein each of the pair of rotation portions comprises a rotation connection portion, and the central body comprises a rotation support portion, and
   wherein a rotation of each of the pair of rotation portions is restricted by an upper portion of the rotation support portion as the rotation connection portion rotates with each of the pair of rotation portions.

7. The spinal plate according to claim 1, wherein a rotation of each of the pair of rotation portions is restricted by a rotational angle control portion formed between a bottom portion of the central body and a bottom portion of each of the pair of rotation portions.

8. The spinal plate according to claim 1, wherein each of the pair of rotation portions comprises a spike screw.

9. The spinal plate according to claim 8, wherein the spike screw comprises a head portion and a body portion, and
   wherein the head portion and the body portion have different threads.

10. The spinal plate according to claim 9, wherein a pitch of the thread in the head portion is smaller than a pitch of the thread in the body portion, thereby enabling self-locking while pulling the vertebrae to the spinal plate.

11. The spinal plate according to claim 8, wherein a washer is put on the bone screw on a washer support part on each of the pair of rotation portions.

12. The spinal plate according to claim 11, wherein the spinal plate is designed such that the washer is configured to rotate with respect to each of the pair of rotation portions and a head of the bone screw is configured to rotate with respect to the washer.

13. The spinal plate according to claim 1, wherein the first angle between each of the pair of rotation portions and the central body is up to 20 degree with respect to the longitudinal direction of the central body.

* * * * *